(12) United States Patent
Ahmad et al.

(10) Patent No.: US 10,369,320 B2
(45) Date of Patent: Aug. 6, 2019

(54) MODULAR VENTILATION SYSTEM

(71) Applicant: Breathe Technologies, Inc., Irvine, CA (US)

(72) Inventors: Samir S. Ahmad, Irvine, CA (US); Enrico Brambilla, Irvine, CA (US); Ali Nikkhah, Irvine, CA (US); Lawrence A. Mastrovich, Irvine, CA (US); Gary Berman, Irvine, CA (US); Masoud Vahidi, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 354 days.

(21) Appl. No.: 15/411,665

(22) Filed: Jan. 20, 2017

(65) Prior Publication Data

US 2017/0209662 A1 Jul. 27, 2017
US 2018/0177968 A2 Jun. 28, 2018

Related U.S. Application Data

(60) Provisional application No. 62/281,415, filed on Jan. 21, 2016.

(51) Int. Cl.
*A61M 16/08* (2006.01)
*A61M 16/00* (2006.01)
(Continued)

(52) U.S. Cl.
CPC .... *A61M 16/0816* (2013.01); *A61M 16/0063* (2014.02); *A61M 16/024* (2017.08);
(Continued)

(58) Field of Classification Search
CPC .......... A61M 16/0057; A61M 16/0063; A61M 16/0066; A61M 16/0069; A61M 16/01;
(Continued)

(56) References Cited

U.S. PATENT DOCUMENTS 5,335,651 A 8/1994 Foster et al.
6,095,138 A * 8/2000 Hognelid .......... A61M 16/0057
128/204.18
(Continued)

FOREIGN PATENT DOCUMENTS

CN 105169537 A 12/2015
WO 2006136878 A1 12/2006

OTHER PUBLICATIONS

Examination Report for AU Application No. 2017209470, dated Nov. 26, 2018.
(Continued)

*Primary Examiner* — Bhisma Mehta
*Assistant Examiner* — James D Ponton
(74) *Attorney, Agent, or Firm* — Stetina Brunda Garred & Brucker

(57) ABSTRACT

Modular ventilatory support systems and methods are disclosed in which a user may transition the system between a stationary configuration, an extended range configuration, and a stand-alone configuration. The modular components of the system include a compressor unit, a ventilator which may dock with the compressor unit, and a patient interface which may be connected to either the compressor unit or the ventilator unit. By rearranging these modular components into different configurations, mobility and duration of use may be optimized to fit the present needs. In the stationary configuration, mobility is most restricted, but duration of use is maximized. In the extended range configuration, mobility is enhanced, with duration of use limited by the battery power of the ventilator. In the stand-alone configuration, mobility is maximized, with duration of use limited by battery power of the ventilator and the quantity of an external gas supply.

20 Claims, 10 Drawing Sheets

(51) Int. Cl.
*A61M 16/12* (2006.01)
*A61M 16/10* (2006.01)
*A61M 16/06* (2006.01)

(52) U.S. Cl.
CPC ........ *A61M 16/06* (2013.01); *A61M 16/1005* (2014.02); *A61M 16/105* (2013.01); *A61M 16/107* (2014.02); *A61M 16/125* (2014.02); *A61M 16/101* (2014.02); *A61M 2202/0208* (2013.01); *A61M 2205/121* (2013.01); *A61M 2205/21* (2013.01); *A61M 2205/3569* (2013.01); *A61M 2205/3592* (2013.01); *A61M 2205/502* (2013.01); *A61M 2205/505* (2013.01); *A61M 2205/581* (2013.01); *A61M 2205/75* (2013.01); *A61M 2205/8206* (2013.01); *A61M 2205/8237* (2013.01); *A61M 2205/8262* (2013.01); *A61M 2209/082* (2013.01); *A61M 2209/088* (2013.01)

(58) Field of Classification Search
CPC .......... A61M 16/0101; A61M 2205/12; A61M 2205/121; A61M 2205/8206; A61M 2209/08; A61M 2209/082; A61M 2209/084; A61M 2209/086; A61M 2209/088; A61B 2560/0443; A61B 2560/045; A61B 2560/0456
See application file for complete search history.

(56) References Cited

U.S. PATENT DOCUMENTS

| | | | |
|---|---|---|---|
| 6,158,430 A | 12/2000 | Pfeiffer et al. | |
| 7,533,670 B1 | 5/2009 | Freitag et al. | |
| 8,381,729 B2 | 2/2013 | Freitag et al. | |
| 8,418,694 B2 | 4/2013 | Freitag et al. | |
| 8,567,399 B2 | 10/2013 | Wondka et al. | |
| 8,770,193 B2 | 7/2014 | Wondka et al. | |
| 8,776,793 B2 | 7/2014 | Wondka et al. | |
| 8,895,108 B2 | 11/2014 | Lee | |
| 9,399,109 B2 | 7/2016 | Baloa Welzien et al. | |
| 2002/0053286 A1 | 5/2002 | Czabala | |
| 2005/0051168 A1 | 3/2005 | DeVries et al. | |
| 2005/0161043 A1* | 7/2005 | Whitley | B01D 53/0473 128/205.18 |
| 2008/0202508 A1 | 8/2008 | McClain et al. | |
| 2012/0298099 A1 | 11/2012 | Lalonde | |
| 2013/0206140 A1 | 8/2013 | Kepler et al. | |
| 2013/0333702 A1 | 12/2013 | Baloa Welzien et al. | |
| 2014/0034055 A1 | 2/2014 | Baloa Welzien et al. | |
| 2014/0137737 A1 | 5/2014 | Wilkinson et al. | |
| 2014/0261426 A1 | 9/2014 | Ahmad et al. | |
| 2014/0283834 A1 | 9/2014 | Ahmad et al. | |
| 2014/0373842 A1 | 12/2014 | Ahmad et al. | |
| 2015/0011905 A1 | 1/2015 | Baloa Welzien et al. | |
| 2015/0068528 A1 | 3/2015 | Ahmad et al. | |
| 2015/0068529 A1 | 3/2015 | Ahmad et al. | |
| 2015/0073291 A1 | 3/2015 | Baloa Welzien et al. | |
| 2015/0165143 A1 | 6/2015 | Baloa et al. | |
| 2015/0231349 A1 | 8/2015 | Ahmad et al. | |
| 2015/0231350 A1 | 8/2015 | Baloa Welzien et al. | |

OTHER PUBLICATIONS

International Search Report and Written Opinion for PCT/US2017/014597, dated Apr. 6, 2017.

Extended European Search Report for P020481 EP-01; dated Mar. 26, 2019.

\* cited by examiner

MODULAR VENTILATION SYSTEM

CROSS-REFERENCE TO RELATED APPLICATIONS

This application relates to and claims the benefit of U.S. Provisional Application No. 62/281,415 filed Jan. 21, 2016 and entitled "MODULAR VENTILATION SYSTEM," the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to ventilators and, more particularly, to a modular ventilation system which is adapted to provide continuous or intermittent ventilatory support for the care of individuals who require mechanical ventilation.

2. Related Art

A wide range of clinical conditions may require some form of ventilation therapy. These conditions may include hypoxemia, various forms of respiratory insufficiency, and airway disorders. There are also non-respiratory and non-airway diseases that require ventilation therapy, such as congestive heart failure and neuromuscular diseases.

To improve the quality of life of many patients who require long-term ventilation therapy, various types of ventilation systems have been developed in the prior art. Some of these prior art systems are compact, lightweight and portable, whereas others are substantially more robust and not well suited for portability or to be wearable by the patient. However, the known prior art is deficient in providing a ventilation system which is uniquely adapted for use in any one of several different configurations, and to provide any one of several different types of ventilatory support corresponding to those configurations. These deficiencies are addressed by the modular ventilation system of the present disclosure, as described in more detail below.

BRIEF SUMMARY

To solve these and other problems, a novel modular ventilation system capable of transitioning between a stationary configuration, an extended range configuration, and a stand-alone configuration, and methods of use thereof for providing continuous or intermittent ventilatory support for the care of individuals who require mechanical ventilation, is contemplated. In greater detail, the modular ventilation system is primarily composed of a ventilator, a compressor unit, and a patient interface, and may be used in at least three different configurations, including a stationary configuration, an extended range configuration, and a stand-alone configuration. In the stationary configuration, the ventilator is docked with the compressor unit with the patient interface connected to the compressor unit for ventilation of a stationary patient. In the extended range configuration, which may enable the patient to engage in localized daily living activities, the ventilator is not docked with the compressor unit, but instead is near the patient, where it receives compressed air from the compressor via a compressed gas supply hose, with the patient interface connected to the ventilator. In the stand-alone configuration, which may enable the patient to engage in non-localized activities, the ventilator is not docked or otherwise connected with the compressor unit, but instead is connected to and receives compressed gas from an external compressed gas source such as an oxygen or air cylinder, or hospital wall source, with the patient interface connected to the ventilator.

According to one contemplated embodiment of the presently disclosed modular ventilatory support apparatus, a modular ventilatory support apparatus may comprise a compressor unit, a ventilator, and a patient interface. The compressor unit may comprise a compressor, a ventilator dock having a ventilator dock compressed gas output port and a ventilator dock ventilation gas inlet port, a compressor unit ventilation gas output port, and a compressor unit compressed gas output port. The ventilator is configured for removable docking to the ventilator dock, with the ventilator comprising a ventilator ventilation gas output port and a ventilator compressed gas inlet port. The patient interface is for receiving ventilation gas and delivering ventilation gas to the patient, and has a patient interface gas inlet port transitionable between placement in fluid communication with the compressor unit ventilation gas output port and placement in fluid communication with the ventilator ventilation gas output port. When transitioned to the stationary configuration, the ventilator is docked at the ventilator dock, the ventilator compressed gas inlet port is in fluid communication with the ventilator dock compressed gas output port, the ventilator ventilation gas output port is in fluid communication with the ventilator dock ventilation gas inlet port, and the patient interface gas inlet port is in fluid communication with the compressor unit ventilation gas output port, such that compressed gas is provided by the compressor unit to the ventilator and ventilation gas is returned to the compressor unit for subsequent output from the compressor unit to the patient interface. When transitioned to the extended range configuration, the ventilator is not docked at the ventilator dock, the ventilator compressed gas inlet port is in fluid communication with the compressor unit compressed gas output port, and the patient interface gas inlet port is in fluid communication with the ventilator ventilation gas output port, such that compressed gas is provided by the compressor unit to the ventilator and ventilation gas is provided by the ventilator to the patient interface without being returned to the compressor unit. When transitioned to the stand-alone configuration, the ventilator is not docked at the ventilation dock, the ventilator compressed gas inlet port is in fluid communication with an external compressed gas source, and the patient interface gas inlet port is in fluid communication with the ventilator ventilation gas output port, such that compressed gas is provided by the external compressed gas source to the ventilator and ventilation gas is provided by the ventilator to the patient interface without passing through the compressor unit.

Additionally, methods of using these embodiments of the presently disclosed modular ventilatory support apparatus are also contemplated. Accordingly, a method of transitioning a modular ventilatory support apparatus from one to another of a stationary configuration, an extended range configuration, and a stand-alone configuration is contemplated, with the method comprising a first step of providing a modular ventilatory support apparatus with the aforementioned components of a compressor unit, a ventilator, and a patient interface, and a second step of transitioning the modular ventilatory support apparatus from one to another of a stationary configuration, an extended range configuration, and a stand-alone configuration. The modular ventilatory support apparatus is transitioned to the stationary configuration when the ventilator is docked at the ventilator dock with the ventilator compressed gas inlet port placed in fluid communication with the ventilator dock compressed gas output port and with the ventilator ventilation gas output port placed in fluid communication with the ventilator dock ventilation gas inlet port, and the patient interface gas inlet port is placed in fluid communication with the compressor unit ventilation gas output port, such that compressed gas is provided by the compressor unit to the ventilator and ventilation gas is returned to the compressor unit for subsequent output from the compressor unit to the patient interface. The modular ventilatory support apparatus is transitioned to the extended range configuration when the ventilator is not docked at the ventilation dock, the ventilator compressed gas inlet port is placed in fluid communication with the compressor unit compressed gas output port, and the patient interface gas inlet port is placed in fluid communication with the ventilator ventilation gas output port, such that compressed gas is provided by the compressor unit to the ventilator and ventilation gas is provided by the ventilator to the patient interface without being returned to the compressor unit. The modular ventilatory support apparatus is transitioned to the stand-alone configuration when the ventilator is not docked at the ventilation dock, the ventilator compressed gas inlet port is placed in fluid communication with an external compressed gas source, and the patient interface gas inlet port is placed in fluid communication with the ventilator ventilation gas output port, such that compressed gas is provided by the external compressed gas source to the ventilator and ventilation gas is provided by the ventilator to the patient interface without passing through the compressor unit.

It is additionally contemplated that the aforementioned and other contemplated embodiments and methods may include certain other aspects. For example, the compressor unit may further comprise a low flow gas input port, which may be a low flow oxygen input port. The compressor may also be additionally or alternatively configured to compress ambient air, and the compressor unit may further include one or more ambient air apertures to introduce ambient air to the compressor. The one or more ambient air apertures may further comprise a filter. The compressor unit compressed gas output port may also comprise a Diameter Index Safety System (DISS) coupling.

It is further contemplated that the ventilator may be electrically powered, and may include a rechargeable battery. As such, the ventilator dock may also be configured to provide electrical power to the ventilator for powering the ventilator and for recharging the rechargeable battery when the ventilator is docked at the ventilator dock. The ventilator may further comprise a user interface and a wireless transmitter, with the compressor unit further comprising a wireless receiver. Consequently, it may be seen that the compressor may be controllable by signal transmission from the wireless transmitter to the wireless receiver initiated by user input at the user interface.

BRIEF DESCRIPTION OF THE DRAWINGS

These and other features and advantages of the various embodiments disclosed herein are better understood with respect to the following descriptions and drawings, in which.

Common reference numerals are used throughout the drawings and the detailed description to indicate the same elements.

DETAILED DESCRIPTION

According to various aspects of the present disclosure, a modular ventilatory support system which may be transitioned between a stationary, an extended range, and a stand-alone configuration, and methods of performing such transitions are contemplated. The modular components of the modular ventilatory support system are contemplated to include at least a compressor unit, a ventilator which may dock with the compressor unit, and a patient interface which may be connected to either the compressor unit or the ventilator unit. Due to their modular nature, these components may be rearranged into at least three different configurations, with such configurations having differing attributes relating to the mobility and potential duration of use. As such, it may be seen that through use of the modular ventilatory support systems and methods contemplated herein, a user may select the most appropriate configuration for the modular ventilatory support system to fit their present needs at any given time, and then may transition the modular ventilatory support system to that configuration, achieving flexibility benefits without requiring the use of multiple different ventilatory support systems. For example, when transitioned to the stationary configuration, mobility is restrictive, but duration of use is maximized. When transitioned to the extended range configuration, mobility is enhanced, with duration of use limited by the battery power of the ventilator. When transitioned to the stand-alone configuration, mobility is maximized, with duration of use limited by the battery power of the ventilator and the quantity of an external gas supply. As such, it may be seen that substantial improvements in a patient's quality of life may be achieved through the presently disclosed modular ventilation system.

Figure 1:
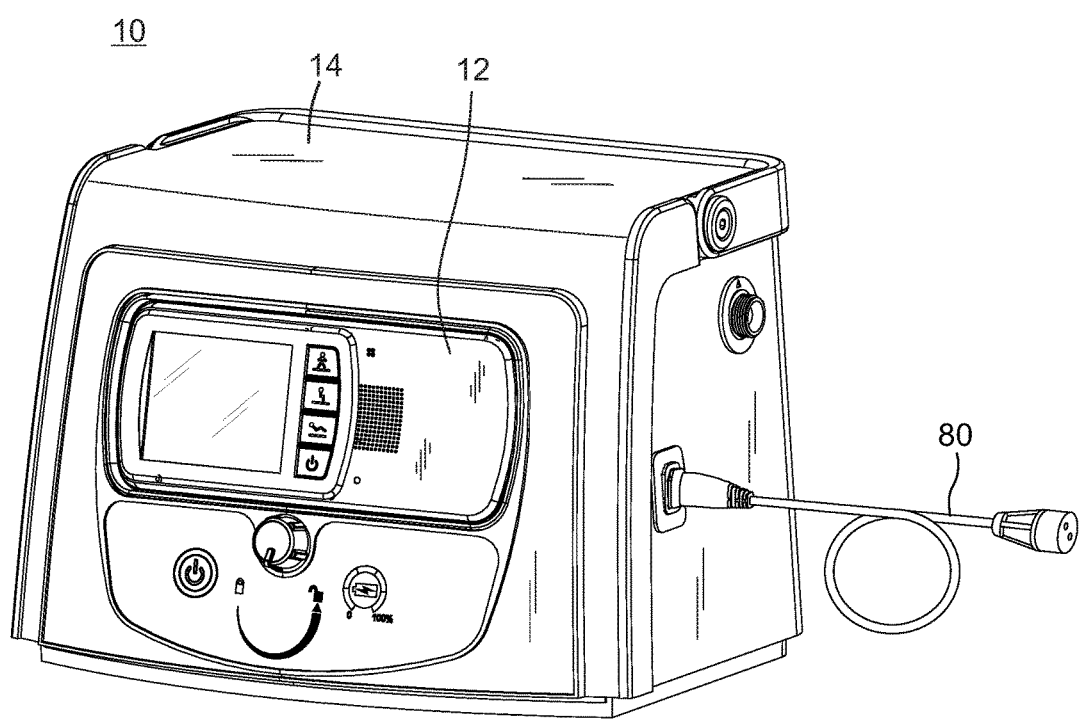
FIG. 1 is a front perspective view of a ventilatory support apparatus in accordance with an embodiment of the disclosed modular ventilation system.

Turning now to FIG. 1, a front perspective view of a ventilatory support apparatus 10 in accordance with an embodiment of the disclosed modular ventilation system is shown. The ventilatory support apparatus 10 may be, for example, in the exemplary embodiment, one or more components of the Breathe Technologies Life2000™ Ventilation System described in Appendix A to this specification, the disclosure of which is incorporated by reference herein. However, it may be seen that the ventilatory support apparatus 10 may be any ventilation system having the herein described components and/or operating according to the herein disclosed methods. In the exemplary embodiment, the ventilatory support apparatus 10 is transitionable between a stationary configuration, an extended range configuration, and a stand-alone configuration. The ventilatory support apparatus 10 includes at least a ventilator 12, a compressor unit 14, and a patient interface 80. In the configuration shown in FIG. 1, i.e. the stationary configuration, the ventilator 12, the compressor unit 14, and the patient interface 80 are used together. However, in other contemplated configurations to which the ventilation system may be transitioned, as described below, the ventilator 12 and the patient interface 80 of the ventilatory support apparatus 10 may be used independently from the compressor unit 14.

The ventilator 12 operates to provide ventilation gas and may be, in the exemplary embodiment, the Breathe Technologies Life2000™ Ventilator described in Appendix A, which can be used with the Breathe Technologies Life2000™ Compressor also described in Appendix A, or with an external compressed gas source, which may be, in some embodiments, a 50-PSI pressure source. The ventilation gas may be any gas breathable by a patient using the ventilatory support apparatus 10, e.g. oxygen or air.

The ventilator 12 may operate according to known methods of receiving compressed gas, generating ventilation gas, and providing that ventilation gas to a patient having need of medical ventilation. However, it is contemplated that, in the exemplary embodiment, the ventilator 12 may be configured and/or operate according to certain known configurations of ventilators and/or methods of regulating and delivering ventilation gas to provide therapeutic respiratory support, which may include, for example, the methods disclosed in Applicant's U.S. Pat. No. 7,533,670 entitled SYSTEMS, METHODS, AND APPARATUS FOR RESPIRATORY SUPPORT OF A PATIENT, the contents of which are incorporated by reference herein; Applicant's U.S. Pat. No. 8,381,729 entitled METHODS AND DEVICES FOR MINIMALLY INVASIVE RESPIRATORY SUPPORT, the contents of which are incorporated by reference herein; Applicant's U.S. Pat. No. 8,418,694 entitled SYSTEMS, METHODS, AND APPARATUS FOR RESPIRATORY SUPPORT OF A PATIENT, the contents of which are incorporated by reference herein; Applicant's U.S. Pat. No. 8,567,399 entitled METHODS AND DEVICES FOR PROVIDING INSPIRATORY AND EXPIRATORY FLOW RELIEF DURING VENTILATION THERAPY, the contents of which are incorporated by reference herein; Applicant's U.S. Pat. No. 8,770,193 entitled METHODS AND DEVICES FOR CONTROLLING VENTILATOR FUNCTIONS, the contents of which are incorporated by reference herein; Applicant's U.S. Pat. No. 8,776,793 entitled METHODS AND DEVICES FOR SENSING RESPIRATION AND CONTROLLING VENTILATOR FUNCTIONS, the contents of which are incorporated by reference herein; Applicant's U.S. Pat. No. 8,895,108 entitled MECHANICAL VENTILATION MASK FIT STATUS INDICATION, the contents of which are incorporated by reference herein; Applicant's U.S. Pat. No. 9,399,109 entitled CONTINUOUS POSITIVE AIRWAY PRESSURE (CPAP) THERAPY USING MEASUREMENTS OF SPEED AND PRESSURE, the contents of which are incorporated by reference herein; Applicant's co-pending U.S. application Ser. No. 13/524,983 (corresponding to U.S. Patent Application Pub. No. 2013/0333702) entitled METHOD AND SYSTEM FOR OPERATING A PATIENT VENTILATION DEVICE, the contents of which are incorporated by reference herein; Applicant's co-pending U.S. application Ser. No. 13/566,902 (corresponding to U.S. Patent Application Pub. No. 2014/0034055) entitled SELECTIVE RAMPING OF THERAPEUTIC PRESSURE IN A PATIENT BREATHING APPARATUS, the contents of which are incorporated by reference herein; Applicant's co-pending U.S. application Ser. No. 13/841,189 (corresponding to U.S. Patent Application Pub. No. 2014/0261426) entitled DUAL PRESSURE SENSOR PATIENT VENTILATOR, the contents of which are incorporated by reference herein; Applicant's co-pending U.S. application Ser. No. 13/849,443 (corresponding to U.S. Patent Application Pub. No. 2014/0283834) entitled PORTABLE VENTILATOR SECRETION MANAGEMENT SYSTEM, the contents of which are incorporated by reference herein; Applicant's co-pending U.S. application Ser. No. 13/927,016 (corresponding to U.S. Patent Application Pub. No. 2014/0373842) entitled VENTILATOR WITH INTEGRATED COOLING SYSTEM, the contents of which are incorporated by reference herein; Applicant's co-pending U.S. application Ser. No. 13/935,362 (corresponding to U.S. Patent Application Pub. No. 2015/0011905) entitled RESPIRATORY CYCLE PATIENT VENTILATION FLOW LIMITATION DETECTION, the contents of which are incorporated by reference herein; Applicant's co-pending U.S. application Ser. No. 14/020,729 (corresponding to U.S. Patent Application Pub. No. 2015/0073291) entitled APNEA AND HYPOPNEA DETECTION, the contents of which are incorporated by reference herein; Applicant's co-pending U.S. application Ser. No. 14/104,842 (corresponding to U.S. Patent Application Pub. No. 2015/0165143) entitled CONTINUOUS POSITIVE AIRWAY PRESSURE THERAPY AUTO-TITRATION, the contents of which are incorporated by reference herein; Applicant's co-pending U.S. application Ser. No. 14/181,431 (corresponding to U.S. Patent Application Pub. No. 2015/0231349) entitled SLEEP DETECTION FOR CONTROLLING CONTINUOUS POSITIVE AIRWAY PRESSURE THERAPY, the contents of which are incorporated by reference herein; and Applicant's co-pending U.S. application Ser. No. 14/181,435 (corresponding to U.S. Patent Application Pub. No. 2015/0231350) entitled DETECTION OF PATIENT INTERFACE DISCONNECT FOR CONTROLLING CONTINUOUS POSITIVE AIRWAY PRESSURE THERAPY, the contents of which are incorporated by reference herein; Applicant's co-pending U.S. application Ser. No. 14/482,444 (corresponding to U.S. Patent Application Pub. No. 2015/0068528) entitled CONTINUOUS POSITIVE AIRWAY PRESSURE THERAPY TARGET PRESSURE COMFORT SIGNATURE, the contents of which are incorporated by reference herein; and Applicant's co-pending U.S. application Ser. No. 14/482,445 (corresponding to U.S. Patent Application Pub. No. 2015/0068529) entitled ZERO PRESSURE START CONTINUOUS POSITIVE AIRWAY PRESSURE THERAPY, the contents of which are incorporated by reference herein.

The compressor unit 14 may be, in the exemplary embodiment, the Breathe Technologies Life2000™ Compressor described in the attached Appendix A, which is an electro-pneumatic power unit that may provide the ventilator 12 with a continuous source of compressed gas and additionally may serve as a charging station for the ventilator 12. It is contemplated that the ventilator 12 and the compressor unit 14 may be configured such that the ventilator 12 may be docked with the compressor unit 14, e.g. by insertion of the ventilator 12 into the compressor unit 14 as shown in FIG. 1. However, it may be seen that the ventilator 12 may be docked with the compressor unit 14 in other fashions other than insertions, and the exact method of docking is not critical, so long as the docking establishes the necessary fluid connections between the ventilator 12 and the compressor unit 14, with such fluid connections being discussed in detail further below. However, those of ordinary skill in the art will recognize that assuming the use of a docking modality involving the insertion of the ventilator 12 into the compressor unit 14, it is contemplated that the shape or form factor of the receptacle or other opening in the compressor unit 14 which accommodates the ventilator 12 will be complimentary to that of the ventilator 12 itself as shown in FIG. 1, thus providing both the functional and visual effects of a smooth, somewhat seamless integration between these two structural features.

Figure 2:
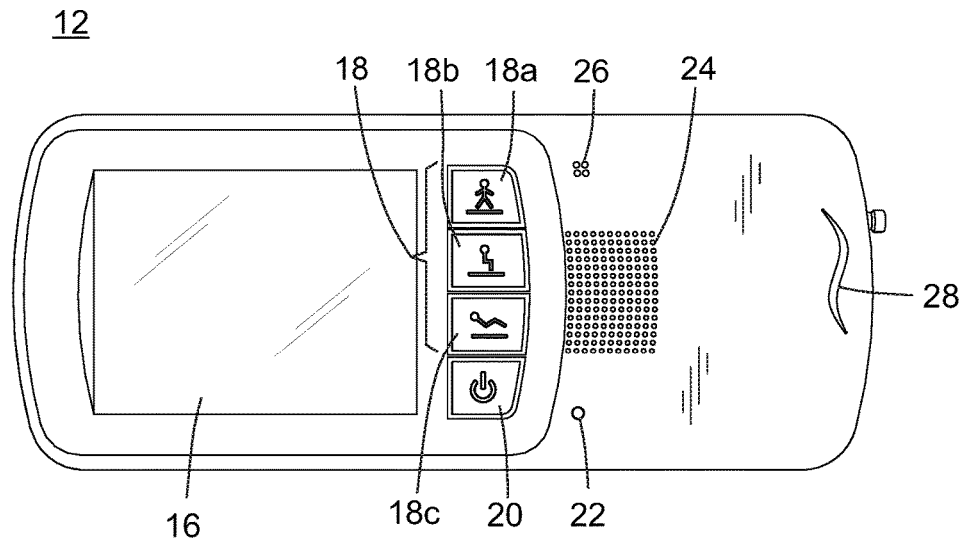
FIG. 2 is a front elevational view of a ventilator of the ventilatory support apparatus.

Turning now to FIG. 2, a front elevational view of a ventilator 12 according to the exemplary embodiment is shown. As shown in the example of FIG. 2, the ventilator 12 may include a user interface 18 comprising, for example, a display 16, a ventilator power button 20, a ventilator power indicator light 22, an alarm speaker 24, a backup alarm speaker 26, and a breath indicator light 28. The user interface 18 may include prescription settings buttons, for example, a high activity button 18a, a medium activity button 18b, and a low activity button 18c, and may further include other buttons, dials, sliders, switches, etc. The display 16 may be a touch screen, in which case the user interface 18 may further include a touch screen functionality of the display 16. It may therefore be seen that the user interface 18 of the ventilator may be configured to receive a user input.

Figure 3:
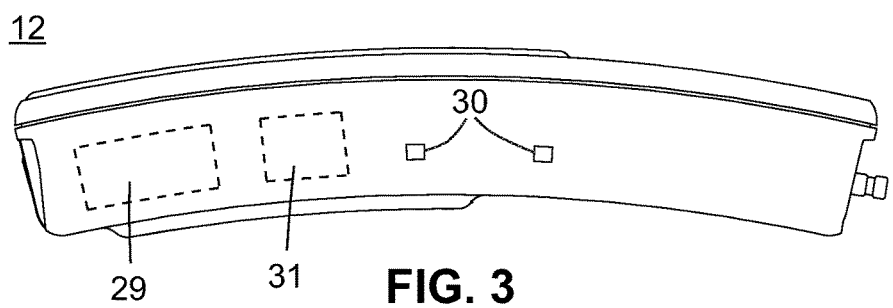
FIG. 3 is a side elevational view of the ventilator.

Turning now to FIG. 3, a side elevational view of the exemplary embodiment of a ventilator 12 is shown. As shown in the embodiment illustrated in FIG. 3, the ventilator 12 may further include other aspects such as belt clip sockets 30 for attachment to a belt clip or other attachment features, in order to support attachment of the ventilator 12 to persons or objects when not docked with the compressor unit 14. The belt clip sockets 30 may be included on both sides of the ventilator 12 (only one side shown in FIG. 3). The ventilator may also include internally a rechargeable battery 29 and a wireless transmitter 31.

Figure 4:
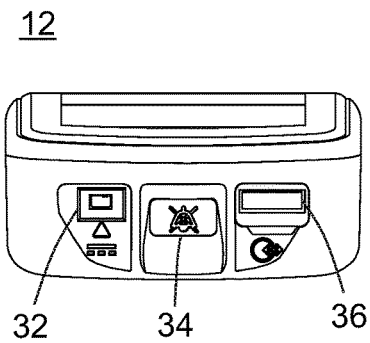
FIG. 4 is a top plan view of the ventilator.

Turning now to FIG. 4, a top plan view of the exemplary embodiment of a ventilator 12 is shown. As shown in the example of FIG. 4, the ventilator 12 may further include a ventilator battery charger connection port 32, a ventilator-side silence alarm button 34, and an additional port 36. The ventilator-side silence alarm button 34 may be used to silence alarms (e.g. as described on pp. 39 and 49 of Appendix A). The additional port 36 may be used by the manufacturer to interface with the ventilator 12, for example, to send and receive data such as firmware updates, predefined operative modes, or error logs. In the exemplary embodiment, the additional port 36 is a USB port. However, in other embodiments, it may be seen that the additional port may be any port known or future developed in the art for interfacing between devices, or may be omitted entirely.

Figure 5:
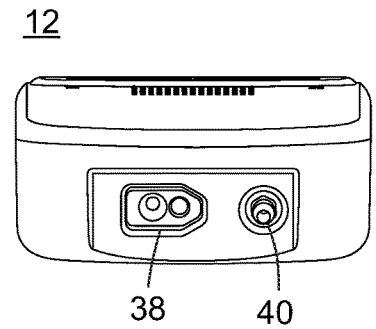
FIG. 5 is a bottom plan view of the ventilator.

Turning now to FIG. 5, a bottom plan view of the exemplary embodiment of a ventilator 12 is shown. As shown in the example of FIG. 5, the ventilator 12 may further include a ventilator ventilation gas output port 38 and a ventilator compressed gas inlet port 40. The ventilator ventilation gas output port 38 may, in the exemplary embodiment, be configured to accept a multi-lumen patient interface gas inlet port 81 of a patient interface 80, such as, for example, the various adapters described in Applicant's co-pending U.S. application Ser. No. 14/020,032 (corresponding to U.S. Patent Application Pub. No. 2015/0068519) entitled JET PUMP ADAPTOR FOR VENTILATION SYSTEM, the contents of which are incorporated by reference herein. Furthermore, the patient interfaces may be, for example, those interfaces described in, for example, Applicant's U.S. Pat. Nos. 8,839,791; 8,844,533; 9,038,634; 9,038,635; 9,132,250; 9,180,270; 9,227,034; and 9,327,092, the contents of which are herein incorporated by reference. However, it may be seen that, in other embodiments, the ventilator ventilation gas output port 38 may be configured in other configurations so as to accept or otherwise fluidly connect to a patient interface gas inlet port 81 of a patient interface 80 for delivering breathing gas to a patient, with possible patient interface 80 including but not being limited to nasal interfaces, nasal masks, respiratory masks, oro-nasal masks, or intubation devices.

Figure 6:
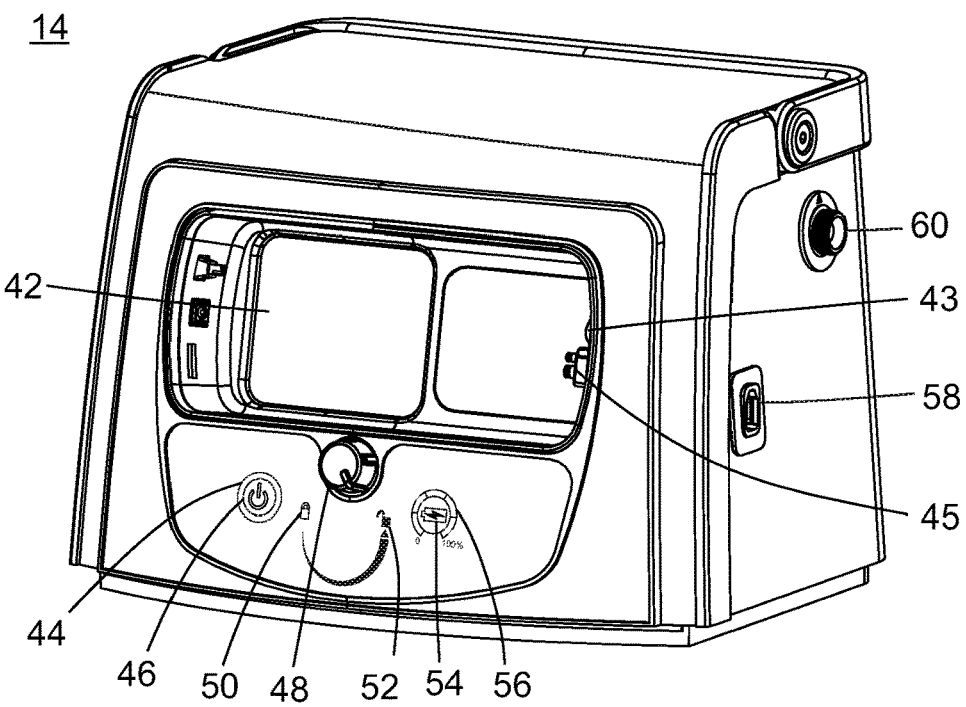
FIG. 6 is a front perspective view of a compressor unit of the ventilatory support apparatus.

Turning now to FIG. 6, a front perspective view of the compressor unit 14 of the exemplary embodiment of the ventilatory support apparatus 10 is shown. As shown in the example of FIG. 6, the compressor unit 14 may include a ventilator dock 42, a compressor power source indicator light 44, a compressor power button 46, a locking knob 48, a locked icon 50, an unlocked icon 52, a battery charge status button 54, a battery charge indicator 56, a compressor unit compressed gas output port 58, and a compressor unit ventilation gas output port 60. The ventilator dock 42 may have a ventilator dock compressed gas output port 43 and a ventilator dock ventilation gas inlet port 45 and may further be configured to provide electrical power for powering the ventilator 12 and for recharging the rechargeable battery 29 of the ventilator 12 when the ventilator 12 is docked at the ventilator dock 42. The ventilator dock compressed gas output port 43 may be configured to interface with the ventilator compressed gas inlet port 40 when the ventilator 12 is docked at the docking port 42 so as to form a generally sealed fluid connection between the two ports. Likewise, the ventilator dock ventilation gas inlet port 45 may be configured to interface with the ventilator ventilation gas output port 38 when the ventilator 12 is docked at the docking port 42 so as to form a generally sealed fluid connection between the two ports. Further, it may be seen that the docking port 42 may additionally include a power conduit for interfacing with the ventilator battery charger connection port 32 of the ventilator 12 so as to provide electrical power to the ventilator 12 when docked at the docking port 42 for powering the ventilator 12 and for charging the rechargeable battery 29. The power conduit may, in certain embodiments, be configured to be spring-loaded or otherwise movable to permit retraction and subsequent insertion or other form of connection to ventilator battery charger connection port 32, such as when the locking knob 48 is actuated, as it may be seen that doing so may more easily permit the insertion of the ventilator 12 into the docking port 42. Those of ordinary skill in the art will recognize that the complimentary, generally quadrangular (i.e., rectangular) configurations of the ventilator 12 as shown in FIGS. 2-5, and it corresponding docking port 42 within the compressor unit 14 are exemplary only, and may be substituted with alternative complementary shapes without departing from the spirit and scope of the present invention.

The locked icon 46 may additionally function as a ventilator charging indicator light. The compressor unit compressed gas output port 58 may, in the exemplary embodiment, be a Diameter Index Safety System (DISS) coupling and may be, e.g., a DISS 1240 output connection port. However, it may be seen that in other embodiments, the compressed gas output port 58 may be any port that is suitable for outputting compressed gas.

Figure 7:
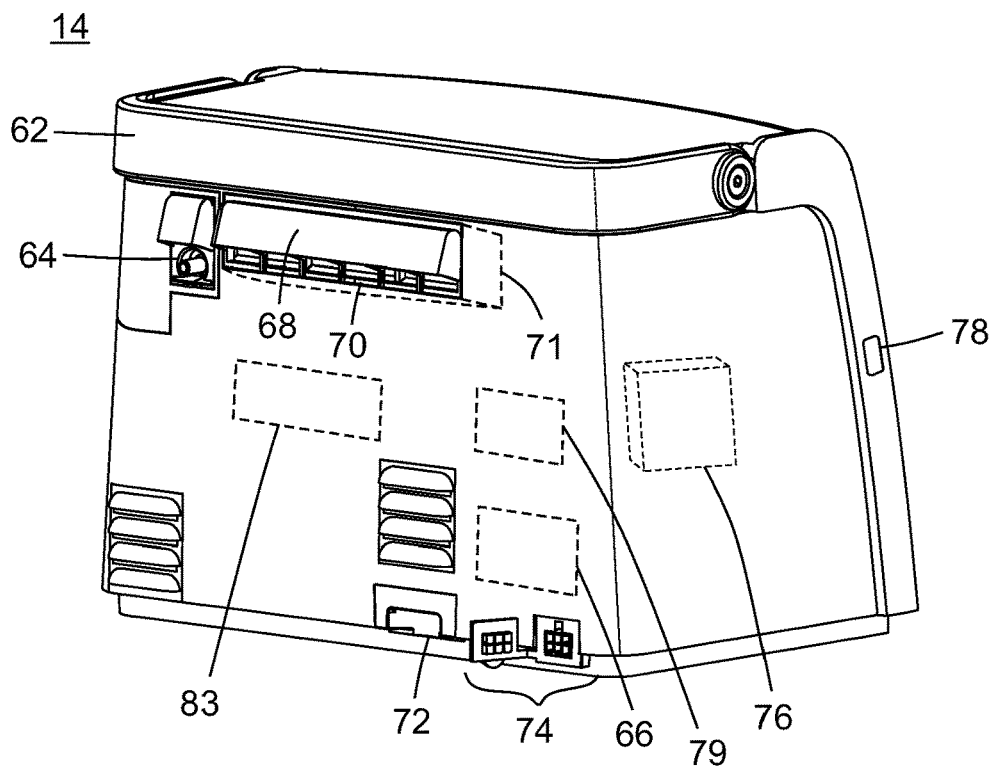
FIG. 7 is a rear perspective view of the compressor unit.

Turning now to FIG. 7, a rear perspective view of the exemplary embodiment of the compressor unit 14 is shown. In the exemplary embodiment, the compressor unit 14 further includes a handle 62, a low flow gas (e.g. oxygen) input port 64, internal battery 66, an ambient air filter cover 68, one or more ambient air apertures 70, a water tray 72, a power supply connection port 74, an alarm speaker 76 (internal), a compressor-side silence alarm button 78, and a wireless receiver 79 (internal), as well as a compressor 83 (internal) for providing compressed gas. The handle 62 may be arranged to ensure that the compressor unit 14 remains in an upright position when carried. The one or more ambient air apertures 70 may include an ambient air filter 71 for preventing particulate matter from entering into the compressor unit. The power supply connection port 74 may include a removable or displaceable cover. The compressor-side silence alarm button 78 may be used to silence alarms (e.g., as described on p. 24 of Appendix A). AC power may be supplied to the compressor unit 14 by connecting an external power supply to the power supply connection port 74 using an AC power cord (e.g., as described on p. 17 of Appendix A).

The compressor 83 may be configured to compress ambient air and/or low-pressure gas and to produce compressed gas for subsequently delivery to the ventilator 12. In the exemplary embodiment, the one or more ambient air apertures 70 may permit introduction of ambient air to the compressor 83 through the ambient air filter 71 to be pressurized by the compressor 83 (e.g., as described on p. 142 of Appendix A). It may also be seen, for example, that low-pressure gas may be introduced via low flow gas input port 64 to the compressor 83, and that such low-pressure gas may substitute for or supplement ambient air.

Figure 8:
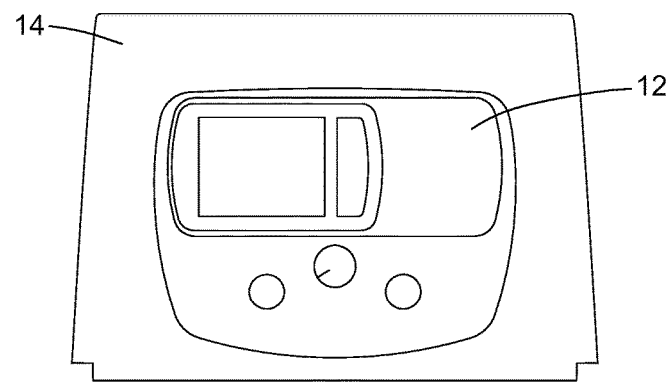
FIG. 8 is a schematic view of the ventilatory support apparatus in the stationary configuration.

Turning now to FIG. 8, a schematic view of the ventilatory support apparatus 10 in the stationary configuration is shown. When the ventilatory support apparatus 10 is in the stationary configuration, the ventilator 12 is docked with the compressor unit 14 while the compressor unit 14 is preferably positioned upright on a flat, level surface.

Figure 9A:
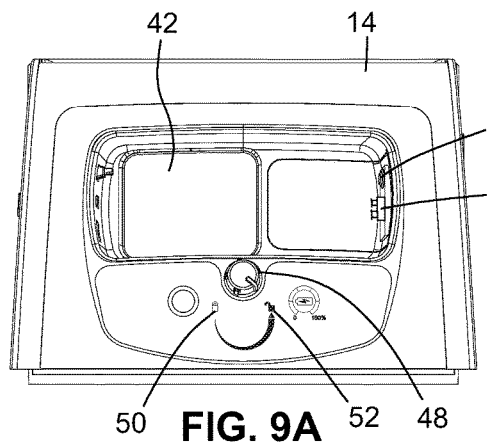
FIGS. 9A-9D are front elevational views (FIGS. 9A and 9D) and enlarged cut-away front perspective views (FIGS. 9B and 9C) of the ventilatory support apparatus transitioning to the stationary configuration in an exemplary process having four steps.
Figure 9B:
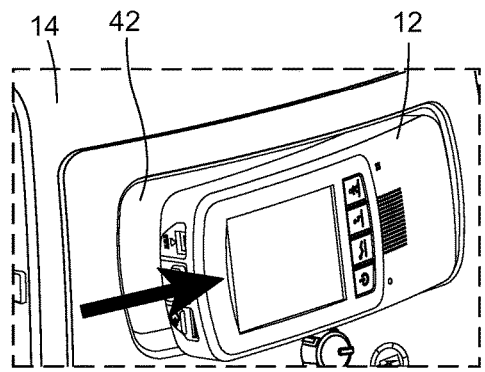
Figure 9C:
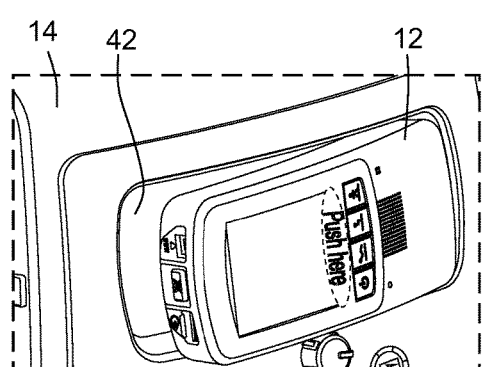
Figure 9D:
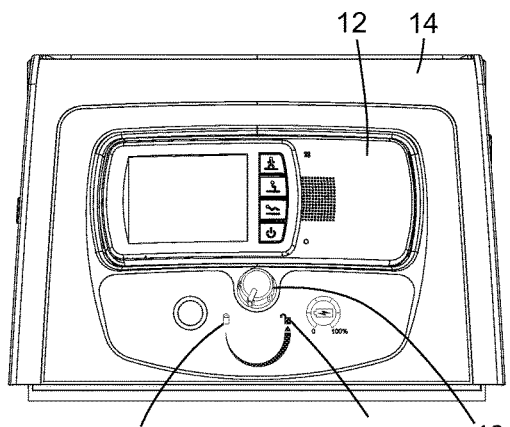

Turning now to FIGS. 9A-9D, front elevational views (FIGS. 9A and 9D) and enlarged cut-away front perspective views (FIGS. 9B and 9C) of the ventilatory support apparatus 10 transitioning to the stationary configuration in the exemplary embodiment are shown in a process having four steps. However, it may be seen that in other embodiments, the process of docking the ventilator 12 at the docking port 42 may differ. According to the exemplary embodiment of the docking process, first, after it is ensured that the ventilator 12 is powered off (the ventilator 12 may be powered off using the ventilator power button 20), it is confirmed that the locking knob 48 on the compressor unit 14 is in the unlocked position as shown in FIG. 9A, e.g., with an appropriate indicator mark on the locking knob 48 facing the unlocked icon 52. Second, as shown in FIG. 9B, the ventilator 12 is positioned in the ventilator dock 42 of the compressor unit 14 with one end (e.g. the bottom end) inserted first as shown, and the ventilator 12 is pushed in the direction of the one end (e.g. the direction of the arrow in FIG. 9B) until the ventilator 12 clicks into place, indicating that the ventilator compressed gas inlet port 40 has been interfaced to form a generally sealed fluid connection with the ventilator dock compressed gas output port 43, and that the ventilator ventilation gas output port 38 has been interfaced to form a generally sealed fluid connection with the ventilator dock ventilation gas inlet port 45. Third, as shown in FIG. 9C, the center of the ventilator 12 is pushed in the direction of the compressor unit 14 (e.g., pushed at "Push here" in FIG. 9C) until the front of the ventilator 12 is flush with the front of the compressor unit 14 and the ventilator 12 clicks into place. Fourth, and finally, as shown in FIG. 9D, the locking knob 48 on the compressor unit 14 is turned to the locked position, e.g. with an appropriate indicator mark on the locking knob 48 facing the locked icon 50. In this way, the ventilator 12 may be docked with the compressor unit 14. As noted above, the locked icon 50 may function as a ventilator charging indicator light. Thus, the locked icon 50 may light up when the compressor unit 14 is powered on and the ventilator 12 is properly docked to indicate that the ventilator 12 is being charged by the compressor unit 14.

Figure 10:
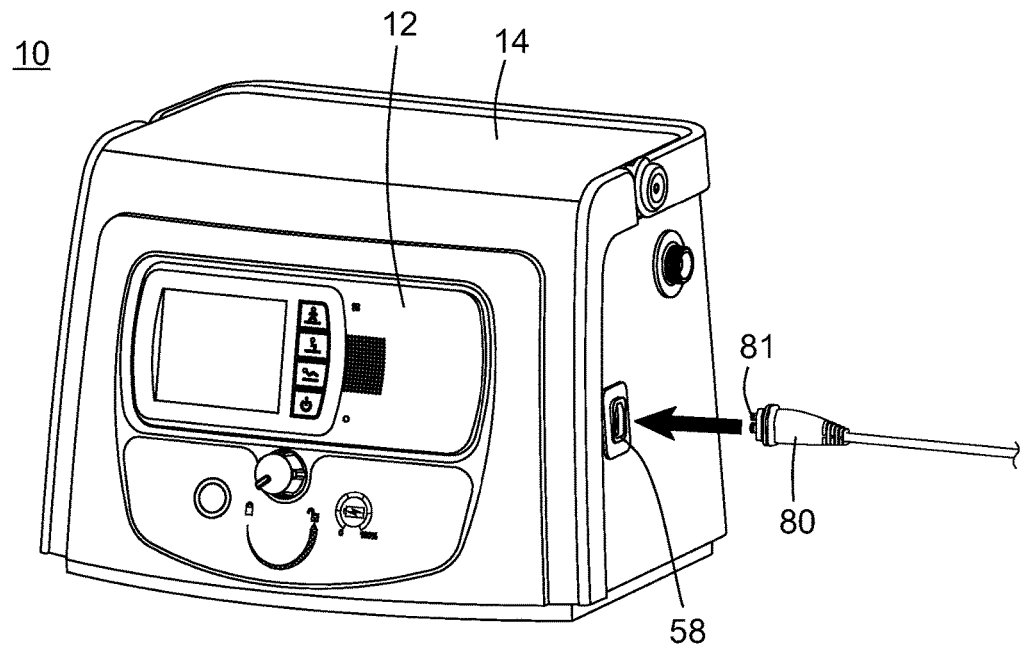
FIG. 10 is a front perspective view of the ventilatory support apparatus in the stationary configuration, including a patient interface.

Turning now to FIG. 10, a front perspective view of the ventilatory support apparatus 10 in the stationary configuration, including the patient interface 80, is shown. The patient interface 80 is for receiving ventilation gas and delivering ventilation gas to a patient and may be any dedicated or universal interface used to connect a non-invasive mask (e.g., full face, nasal, pillows) or tracheostomy tube to the ventilatory support apparatus 10 or ventilator 12. The patient interface 80 may be, for example, in the exemplary embodiment, the Breathe Technologies Universal Circuit™ interface. The patient interface 80 has a patient interface gas inlet port 81 transitionable between placement in fluid communication with the compressor unit compressed gas output port 58 of the compressor unit 14 and placement in fluid communication with the ventilator ventilation gas output port 38 of the ventilator 12. As shown in FIG. 10, when the ventilatory support apparatus 10 is in the stationary configuration, the patient interface 80 may be plugged into the compressor unit compressed gas output port 58.

Figure 11:
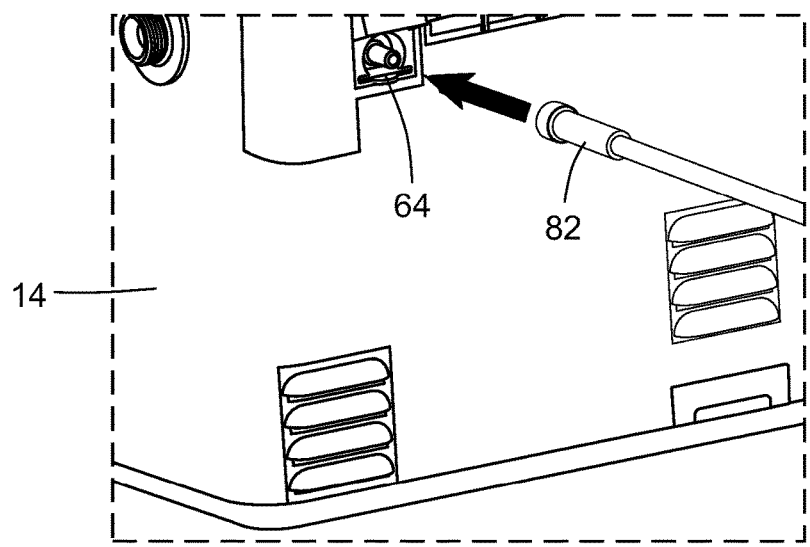
FIG. 11 is an enlarged cut-away rear perspective view of the ventilatory support apparatus in the stationary configuration, along with oxygen connecting tubing.

Turning now to FIG. 11, an enlarged cut-away rear perspective view of the ventilatory support apparatus 10 in the stationary configuration, along with low-flow gas tubing 82, is shown. When using a prescription setting that uses oxygen as the source gas, a low flow supplemental oxygen source (not shown), such as a stationary oxygen concentrator, may be connected to the compressor unit 14. As shown in FIG. 11, one end of the oxygen connecting tubing 82 may be attached to the low flow gas input port 64, e.g., by pushing and turning the oxygen connecting tubing 82 until it is completely and securely attached. The other end of the oxygen connecting tubing 82 may be connected to the low flow supplemental oxygen source, which may then be turned on.

With the ventilatory support apparatus 10 in the stationary configuration, the compressor unit 14 may be powered on by pressing the compressor power button 46, upon which the compressor power source indicator light 44 may illuminate to indicate the power source. For example, green illumination of the compressor power source indicator light 44 may indicate that the compressor is connected to AC power (e.g., by connection to an external power supply via the power supply connection port 74 and an AC power cord), while orange illumination of the compressor power source indicator light 44 may indicate that the compressor is using internal battery power as described below. According to the powering on sequence of the exemplary embodiment, the ventilator 12 is powered on by pressing the ventilator power button 20, upon which the ventilator power indicator light 22 may illuminate. After power on of the compressor unit 14 and ventilator 12, various tests (e.g., a test of the alarm speaker) may be performed and startup screens may be displayed on the display 16, with the display 16 eventually displaying a "Home" screen (e.g., as described on p. 21 of Appendix A).

The compressor unit 14 may include an internal battery 66 for alleviating temporary power disruptions. The internal battery 66 of the compressor unit 14 may charge when the compressor unit 14 is connected to AC power (e.g., by connection to an external power supply via the power supply connection port 74 and an AC power cord). The internal battery 66 of the compressor unit 14 may have a maximum charge, e.g., two hours. The battery charge indicator 56 may include a series of indicator lights arranged as a battery charge scale, e.g., surrounding the battery charge status button 54, the battery charge scale indicating the current battery charge level of the compressor unit 14 (e.g., as described on pp. 22-23 of Appendix A). The battery charge status button 54 may be used, for example to illuminate the battery charge indicator 56 when the compressor unit 14 is powered off.

When the ventilatory support apparatus 10 is transitioned to the stationary configuration, the ventilator 12 is docked at the ventilator dock 42 of the compressor unit 14, the ventilator compressed gas inlet port 40 is in fluid communication with the ventilator dock compressed gas output port 43, the ventilator ventilation gas output port 38 is in fluid communication with the ventilator dock ventilation gas inlet port 45, and the patient interface gas inlet port 81 of the patient interface 80 is in fluid communication with the compressor unit ventilation gas output port 60, such that compressed gas is provided by the compressor unit 14 to the ventilator 12 and ventilation gas is returned to the compressor unit 14 for subsequent output from the compressor unit 14 to the patient interface 80, e.g., via the compressor unit ventilation gas output port 60.

With the ventilatory support apparatus 10 in the stationary configuration, the compressor unit 14 may be powered off by pressing the compressor power button 46. According to the preferred powering off sequence, the ventilator 12 may then be powered off by using the ventilator power button 20, e.g., by pressing the ventilator power button 20 for three seconds and confirming power off using the display 16 (e.g., as described on p. 25 of Appendix A).

Figure 12:
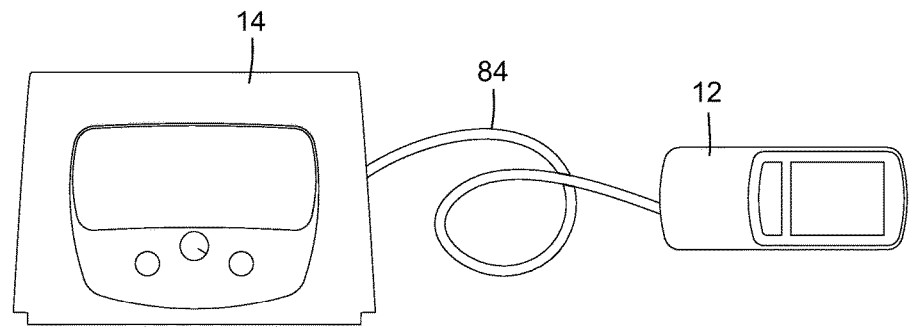
FIG. 12 is a schematic view of the ventilatory support apparatus in the extended range configuration.

Turning now to FIG. 12, a schematic view of the ventilatory support apparatus 10 in the extended range configuration is shown. As noted above, the ventilatory support apparatus 10 may be used in different configurations of operation as the patient's needs change. In the extended range configuration, the ventilator 12 is connected to the compressor unit 14 with a compressed gas hose 84 to enable the activities of daily living. The compressed gas hose 84 may be, for example, a high-pressure hose of any length, e.g., six feet or fifty feet. In the exemplary embodiment, the compressed gas hose 84 connects to the compressor unit compressed gas output port 58 of the compressor unit 14 and to the ventilator compressed gas inlet port 40 of the ventilator 12 via DISS fittings. However, it may be seen that in other embodiments of a ventilatory support apparatus 10 in the extended range configuration, the compressed gas hose 84 may connect the compressor unit compressed gas output port 58 to the ventilator compressed gas inlet port 40 according to any known or future developed method.

Figure 13A:
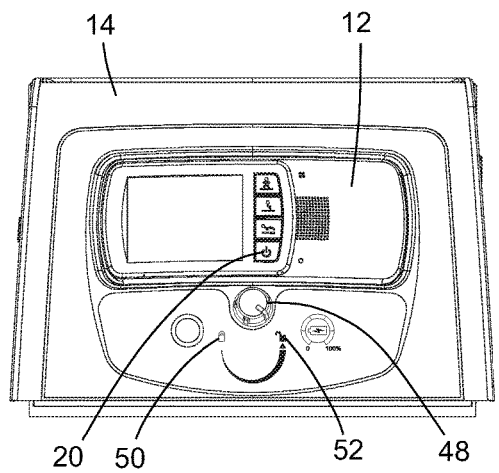
FIGS. 13A and 13B are a front elevational view and an enlarged cut-away front perspective view, respectively, of the ventilatory support apparatus transitioning from the stationary configuration by an exemplary process having two steps.
Figure 13B:
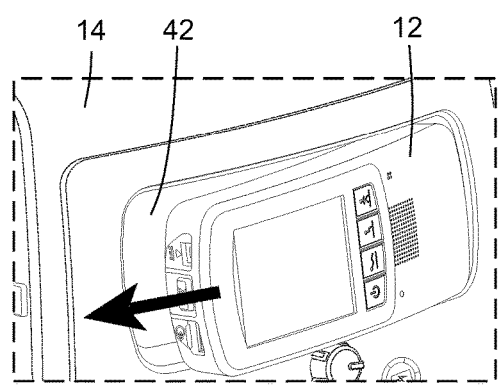

Turning now to FIGS. 13A and 13B, a front elevational view and an enlarged cut-away front perspective view of the ventilatory support apparatus 10 transitioning away from the stationary configuration according to the exemplary embodiment is shown in two steps. First, after it is ensured that the ventilator 12 is powered off (the ventilator 12 may be powered off using the ventilator power button 20), the locking knob 48 on the compressor unit 14 is turned to the unlocked position as shown in FIG. 13A, e.g., with an appropriate indicator mark on the locking knob 48 facing the unlocked icon 52, at which point the compressor unit 14 will eject the ventilator 12. Second, and finally, as shown in FIG. 13B, the ventilator 12 is pulled in a direction to remove the remaining inserted end of the ventilator 12 (e.g., the bottom end) from the ventilator dock 42 of the compressor unit 14 (e.g., pulled in the direction of the arrow in FIG. 13B) until the ventilator 12 is separated from the ventilator dock 42 of the compressor unit 14. In this way, the ventilator 12 may be undocked from the compressor unit 14.

Figure 14:
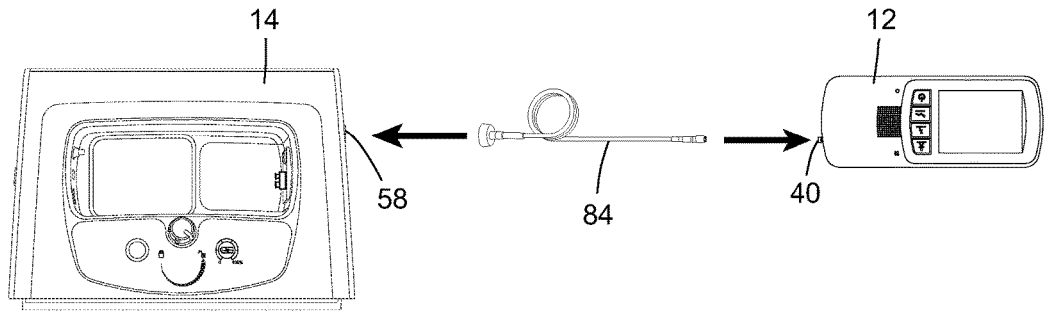
FIG. 14 is a schematic view of the connection of the ventilator to the compressor unit via the compressed gas hose in the extended range configuration.

Turning now to FIG. 14, a schematic view of the connection of the ventilator 12 to the compressor unit 14 via the compressed gas hose 84 in the extended range configuration according to the exemplary embodiment is shown. Connecting the ventilator 12 to the compressor unit 14 via the compressed gas hose 84 allows use of the ventilator 12 without the ventilator 12 having to be docked with the compressor unit 14. According to the preferred connecting sequence, it is first ensured that the ventilator 12 is powered off, whereas the compressor unit 14 may be powered off or powered on. The ventilator 12 is then undocked from the compressor unit 14, e.g., by the example method described with respect to FIG. 13. The compressed gas hose 84 is then attached to the compressor unit compressed gas output port 58. For example, in the exemplary embodiment where the compressor unit compressed gas output port 58 is a DISS 1240 output connection port, the compressed gas hose may be connected to the compressor unit compressed gas output port 58 via a DISS connection on the compressed gas hose 84. Lastly, the other end of the compressed gas hose 84 is connected to the ventilator compressed gas inlet port 40 of the ventilator 12, e.g., by pushing a small quick connect end onto the ventilator compressed gas inlet port 40 until it clicks into place.

Figure 15:
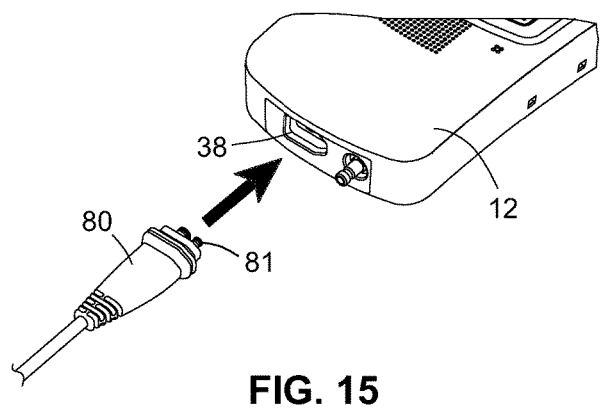
FIG. 15 is a cut-away front perspective view of the ventilator, showing the bottom of the ventilator, including the patient interface.

Turning now to FIG. 15, a cut-away front perspective view of the ventilator 12, showing the bottom of the ventilator 12, along with the patient interface 80, is shown. As shown in FIG. 15, in the extended range configuration, the patient interface 80 may be plugged into the ventilator ventilation gas output port 38.

In the exemplary embodiment, when the ventilatory support apparatus 10 is in the extended range configuration, the compressor unit 14 may be powered on by pressing the compressor power button 46, upon which the compressor power source indicator light 44 may illuminate to indicate the power source in the same way as when the ventilatory support apparatus 10 is in the stationary configuration. For example, green illumination of the compressor power source indicator light 44 may indicate that the compressor is connected to AC power (e.g., by connection to an external power supply via the power supply connection port 74 and an AC power cord), while orange illumination of the compressor power source indicator light 44 may indicate that the compressor is using internal battery power as described below. Continuing the exemplary powering on sequence, the ventilator 12 may then be powered on by pressing the ventilator power button 20 in the same way as when the ventilatory support apparatus 10 is in the stationary configuration, upon which the ventilator power indicator light 22 may illuminate. After power on of the compressor unit 14 and ventilator 12, various tests (e.g., a test of the alarm speaker) may be performed and startup screens may be displayed on the display 16, with the display 16 eventually displaying a "Home" screen (e.g. as described on p. 33 of Appendix A). As noted above, the compressor unit 14 may include an internal battery 66 for temporary power disruptions. The behavior of the internal battery 66 of the compressor unit 14, battery charge indicator 56, and battery charge status button 54 may be the same in the extended range configuration as in the stationary configuration. However, it may be seen that the compressor unit 14 may be powered on or off in alternative ways, such as, for example, by user input at the user interface 18 of the ventilator 12, wherein a wireless transmitter 31 of the ventilator 12 may communicate with the wireless receiver 79 of the compressor unit 14.

The ventilator 12 may also include a rechargeable battery 29 for use while undocked from the compressor unit 14, e.g., while the ventilatory support apparatus 10 is in the extended range configuration. The rechargeable battery 29 of the ventilator 12 may charge while the ventilator 12 is docked with the compressor unit 14, which may function as a charging station for the ventilator 12 as noted above. The rechargeable battery 29 of the ventilator 12 may also be charged in other ways, such as via a ventilator battery charger 86 connecting the ventilator battery charger connection port 32 to a power source such as a wall outlet or a generator. The rechargeable battery 29 of the ventilator 12 may have a maximum charge, e.g., four hours, and may take approximately three to four hours to fully recharge whether the ventilator 12 is off or on. When the ventilator 12 is powered on (e.g., via the ventilator power button 20, the ventilator power indicator light 22 being illuminated), a ventilator battery charge icon on the display 16 may show the current battery charge level of the rechargeable battery 29 of the ventilator 12 (e.g. as described on p. 36 of Appendix A).

Figure 16:
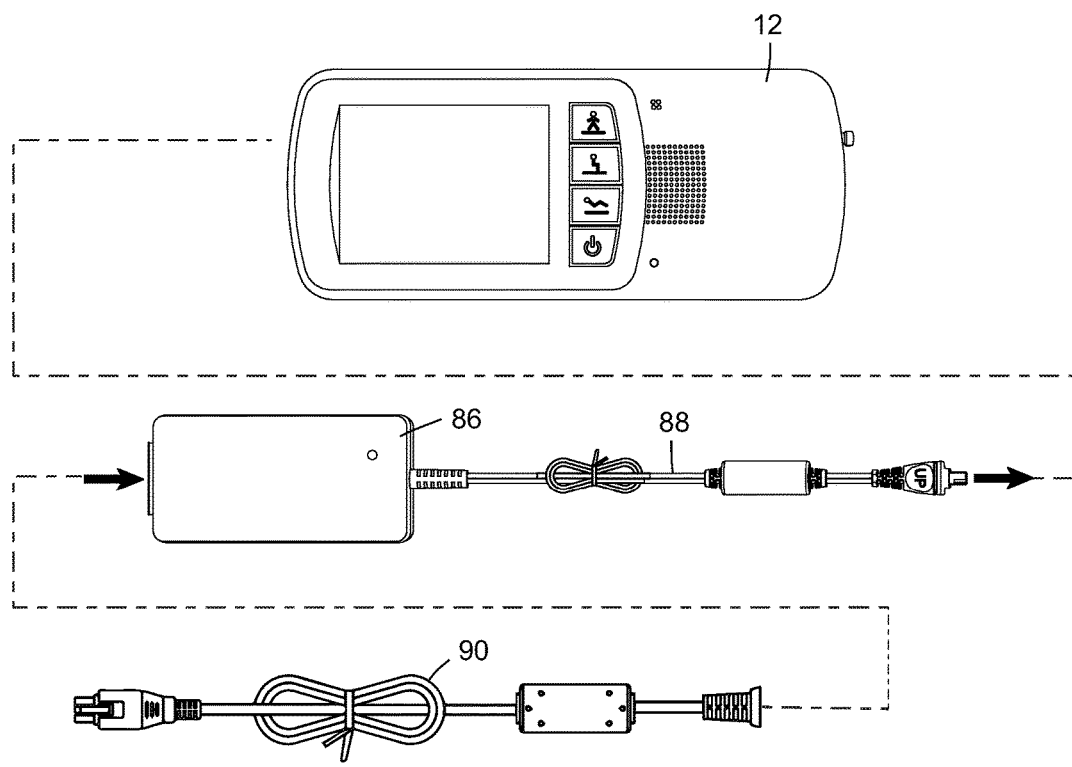
FIG. 16 is a schematic view of the connection of the ventilator to a ventilator battery charger via a ventilator battery charger cord.

Turning now to FIG. 16, a schematic view of the connection of the ventilator 12 to the ventilator battery charger 86 via the ventilator battery charger cord 88 is shown. The ventilator battery charger cord 88 may be integrally or removably connected to the ventilator battery charger 86. Connecting the ventilator 12 to the ventilator battery charger 86 allows charging of the internal battery of the ventilator 12 without the ventilator 12 having to be docked with the compressor unit 14. According to the preferred connecting sequence, a ventilator AC power cord 90 is first connected to the ventilator battery charger 86 and thereafter plugged into an AC power source. Then, the ventilator battery charger cord 88 (which is already connected to the ventilator battery charger 86) is connected to the ventilator battery charger connection port 32 of the ventilator 12 (e.g., as described on p. 37 of Appendix A).

Figure 17A:
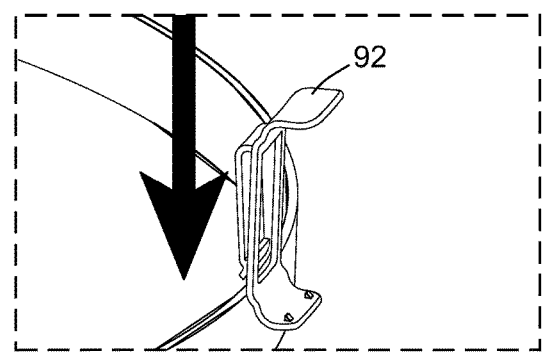
FIGS. 17A and 17B are perspective views showing the ventilator being attached to a belt clip in an exemplary process having two steps.
Figure 17B:
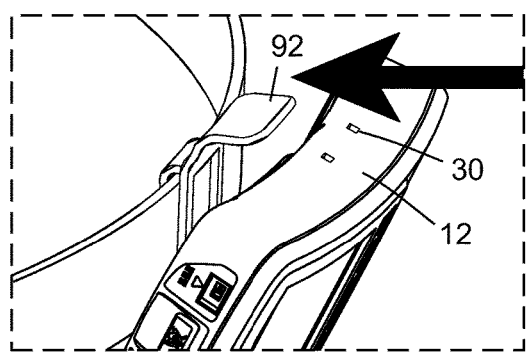

Turning now to FIGS. 17A and 17B, perspective views showing the ventilator 12 being attached to the belt clip 92 in an example process having the two steps is shown. The belt clip 92 may be used to secure the ventilator 12 so as to be wearable on a belt or waistband and may, for example, include protrusions corresponding to the belt clip sockets 30 on the ventilator 12. First, as shown in FIG. 17A, the belt clip 92 is securely fastened to a belt or waistband by positioning the belt clip 92 over the belt or waistband and pushing down (e.g. the direction of the arrow in FIG. 17A) until the belt clip 92 is secure. Second, and lastly, as shown in FIG. 17B, the belt clip 92 may be lined up with the belt clip sockets 30 on the ventilator 12, and the ventilator 12 may be pushed toward the belt clip 92 until a connection is made, e.g., until the protrusions on the belt clip 92 enter the belt clip sockets 30 on the ventilator 12, causing an audible click. In this way, the ventilator 12 may be wearable while the ventilatory support apparatus 10 is in the extended range configuration. Alternatively, the ventilator 12 may, in the extended range configuration, be mounted to a pole mount 94 as described below with respect to the stand-alone configuration. However, it may be seen that there may be a multitude of schemes for mounting or otherwise using the ventilator 12 in the configurations in which it is not docked with the compressor unit 14, and as such the specific illustrated methods should not be construed as limiting the scope of the present disclosure.

When the ventilatory support apparatus 10 is transitioned to the extended range configuration, the ventilator 12 is not docked at the ventilator dock 42, the ventilator compressed gas inlet port 40 is in fluid communication with the compressor unit compressed gas output port 58, and the patient interface gas inlet port 81 of the patient interface 80 is in fluid communication with the ventilator ventilation gas output port 38, such that compressed gas is provided by the compressor unit 14 to the ventilator 12 and ventilation gas is provided by the ventilator 12 to the patient interface 80 without being returned to the compressor unit 14.

With the ventilatory support apparatus 10 in the extended range configuration, the ventilator 12 of the exemplary embodiment may be powered off by pressing the ventilator power button 20, which in the exemplary embodiment may be performed by pressing the ventilator power button 20 for three seconds and confirming power off using the display 16 (e.g., as described on p. 40 of Appendix A). According to the exemplary powering off sequence, the compressor unit 14 may then be powered off by using the compressor power button 46. With the ventilator 12 powered off, the extended range configuration can be terminated by disconnecting the compressed gas hose 84 from the ventilator 12 and the compressor unit 14 (e.g., as described on p. 41 of Appendix A).

Figure 18:
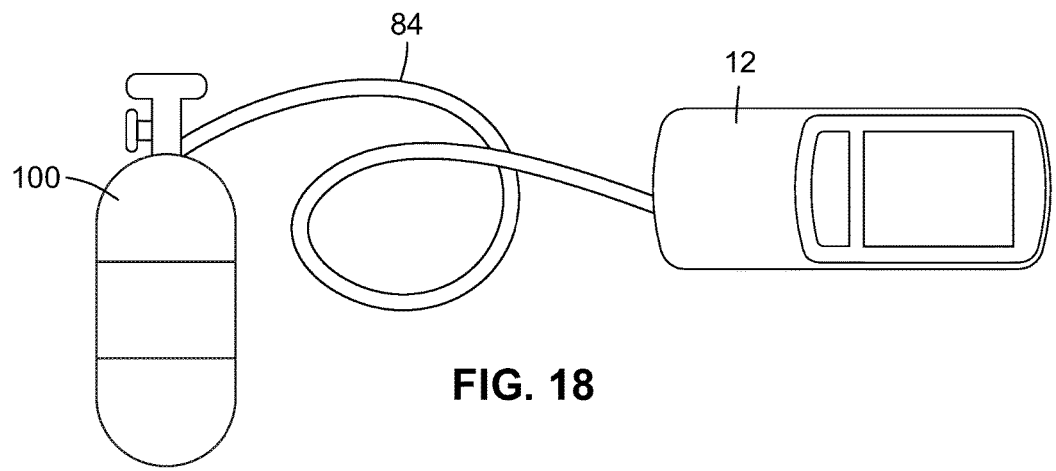
FIG. 18 is a schematic view of the ventilatory support apparatus in the stand-alone configuration.

Turning now to FIG. 18, a schematic view of the ventilatory support apparatus 10 in the stand-alone configuration is shown. As noted above, the ventilatory support apparatus 10 may be used in different configurations of operation as the patient's needs change. In the exemplary embodiment of the stand-alone configuration, the ventilator 12 is connected via the compressed gas hose 84 to an external compressed gas source 100, e.g. an air or oxygen gas cylinder (50-PSI and/or ≤40 LPM at 41 PSI) or wall connection. However, it may be seen that in other embodiments, the external compressed gas source 100 may include any source of compressed gas suitable for use with a ventilator 12. In the exemplary embodiment, the ventilator 12 may be compatible with medical grade compressed air or oxygen. However, it may be seen that in certain embodiments, the ventilator 12 may be only suitable for use with one or the other, or with other compressed gases or blends of compressed gases.

When the ventilatory support apparatus 10 is transitioned from the stationary configuration to the stand-alone configuration, the ventilator 12 may be undocked from the compressor unit 14 in the same way as described above with respect to FIGS. 13A and 13B regarding transitioning to the extended range configuration. In the exemplary embodiment of the stand-alone configuration, after the ventilator 12 is undocked in this way, the compressor unit 14 may be powered off using the compressor power button 46.

With the ventilatory support apparatus 10 in the stand-alone configuration, the ventilator 12, in the exemplary embodiment, may then be powered on by pressing the ventilator power button 20 in the same way as when the exemplary ventilatory support apparatus 10 is in the stationary configuration or the extended range configuration, upon which the ventilator power indicator light 22 may illuminate. After power on of the compressor unit 14 and ventilator 12, various tests (e.g., a test of the alarm speaker) may be performed and startup screens may be displayed on the display 16, with the display 16 eventually displaying a "Home" screen (e.g., as described on p. 44 of Appendix A). As noted above, the ventilator 12 may include an internal battery 66 for use while undocked from the compressor unit 14, e.g. while the ventilatory support apparatus 10 is in the extended range configuration or the stand-alone configuration. The behavior of the internal battery 66 of the ventilator 12 and ventilator battery charge icon on the display 16, as well as the use of the ventilator battery charger connection port 32, ventilator battery charger 86, ventilator battery charger cord 88, and ventilator AC power cord 90, may be the same in the stand-alone configuration as in the extended range configuration (e.g., as described on pp. 45-46 of Appendix A). Moreover, in the stand-alone configuration, the patient interface 80 may be plugged into the ventilator ventilation gas output port 38 in the same way as shown in FIG. 15 and described with respect to extended range configuration.

With the ventilatory support apparatus 10 in the stand-alone configuration, the ventilator 12 may be wearable on a belt or waistband via the belt clip 92 in the same way as described above with respect to FIGS. 17A and 17B. Alternatively, in either the stand-alone configuration or the extended range configuration, the belt clip 92 may also be used to secure the ventilator 12 to a pole via a pole mount 94 as described below. However, it may also be seen that other methods of securing the ventilator 12 and locations where it may be secured may be achieved, without departing from the scope of the disclosure.

Figure 19A:
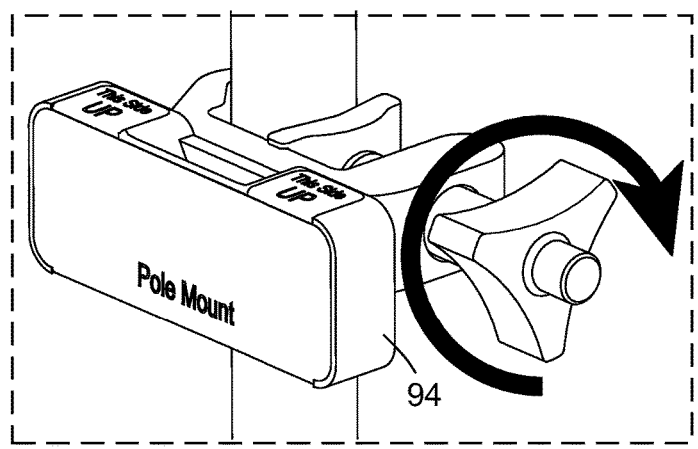
FIGS. 19A-19C are perspective views showing the ventilator being secured to a pole via the belt clip and a pole mount in an exemplary process having three steps.
Figure 19B:
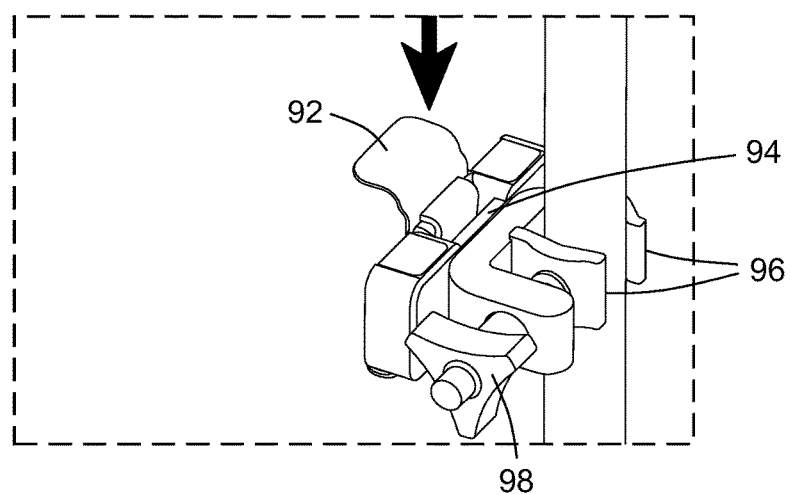
Figure 19C:
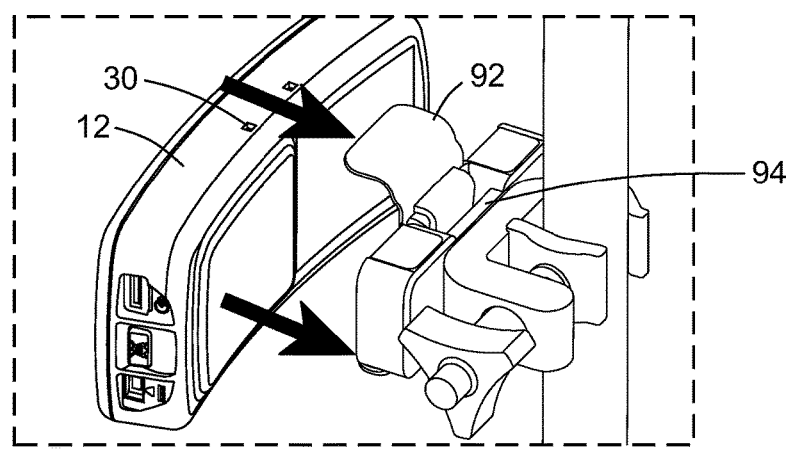

Turning now to FIGS. 19A-19C, perspective views showing an exemplary embodiment of the ventilator 12 being secured to a pole via the belt clip 92 and the pole mount 94 in an process having three steps are shown. First, as shown in FIG. 19A, the pole mount 94 is positioned around the pole in the desired orientation and secured to the pole. In the example shown in FIGS. 19A-19C, the pole mount 94 includes a vice clamp 96 that can be tightened around a pole by turning a knob 98, thereby securing the pole mount 94 to the pole. Second, as shown in FIG. 19B, the belt clip 92 is slid into a hole on the top of the pole mount 94 and pushed down (e.g., in the direction of the arrow shown in FIG. 19B) until secure. Third, and finally, the belt clip 92 is lined up with the belt clip sockets 30 on the ventilator 12, and the ventilator 12 is pushed toward the belt clip 92 until a connection is made, e.g., until the protrusions on the belt clip 92 enter the belt clip sockets 30 on the ventilator 12, causing an audible click.

Figure 20A:
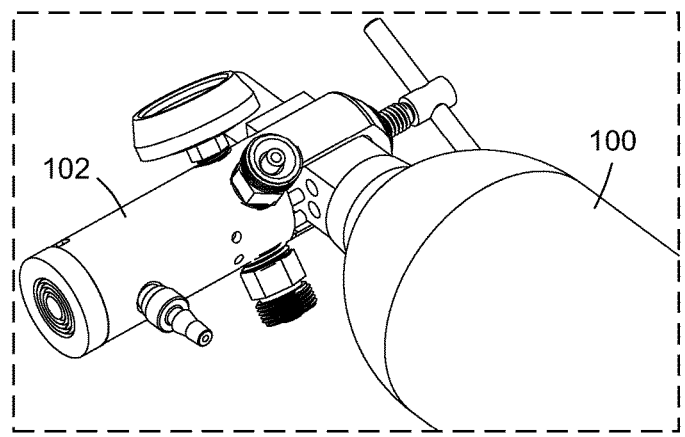
FIGS. 20A-20C are perspective views (FIGS. 20A and 20B) and a top plan view (FIG. 20C) of the ventilatory support apparatus transitioning to the stand-alone configuration by connection of the ventilator to an external compressed gas source in an exemplary process having three steps.
Figure 20B:
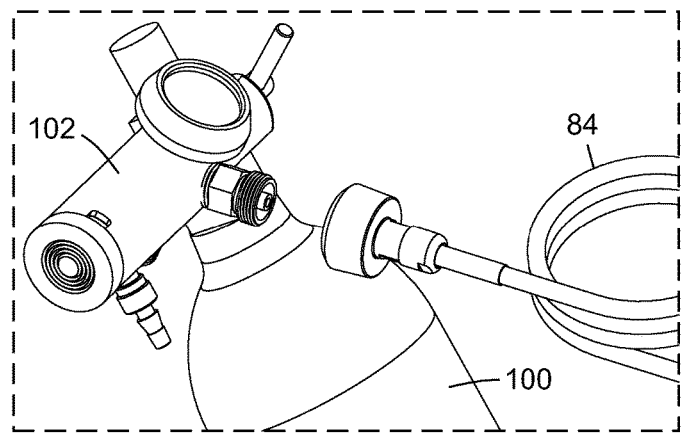
Figure 20C:
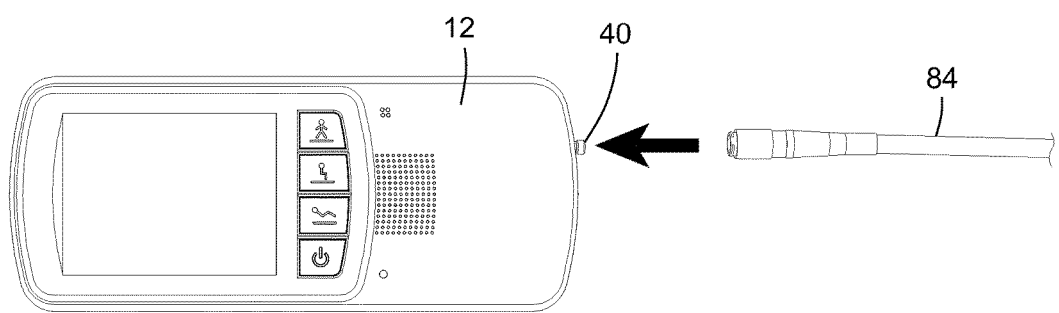

Turning now to FIGS. 20A-20C, perspective views (FIGS. 20A and 20B) and a top plan view (FIG. 20C) of the exemplary embodiment the ventilatory support apparatus 10 transitioning to the stand-alone configuration by connection of the ventilator 12 to an external compressed gas source 100 in an example process having three steps are shown. First, with the ventilator 12 powered off (the ventilator 12 may be powered off using the ventilator power button 20), an oxygen regulator 102 is connected to the external compressed gas source 100 as shown in FIG. 20A, e.g., by sliding the oxygen regulator 102 over the neck of an oxygen cylinder (external compressed gas source 100), lining up pins on the oxygen regulator 102 with holes on the neck, and tightening a tee screw on the oxygen regulator 102 by turning a handle. Second, as shown in FIG. 20B, the compressed gas hose 84 is connected to the oxygen regulator 102, e.g. to a DISS connector end of the oxygen regulator 102. Third, and finally, as shown in FIG. 20C, after turning on the gas supply according to the preferred usage method of the external compressed gas source 100 and oxygen regulator 102, the other end of the compressed gas hose 84 is connected to the ventilator 12, e.g., by pushing the small quick connect end onto the ventilator compressed gas inlet port 40 until it clicks into place. The external compressed gas source 100 may thereafter be replaced, e.g., as described on p. 53 of Appendix A.

In the exemplary embodiment illustrated in FIGS. 20A-20C, the external compressed gas source 100 is an oxygen cylinder and the compressed gas hose 84 and oxygen regulator 102 are used. However, it may be seen that in other embodiments, the external compressed gas source 100 may be different, e.g., another gas or gas blend other than oxygen, a portable gas compressor, or another oxygen source such as an oxygen concentrator. If the external compressed gas source 100 is an air cylinder, another hose such as an air hose may be used in place of the compressed gas hose 84 and another appropriate regulator may be used in place of the oxygen regulator 102.

When the ventilatory support apparatus 10 is transitioned to the stand-alone configuration, the ventilator 12 is not docked at the ventilator dock 42, the ventilator compressed gas inlet port 40 is in fluid communication with an external compressed gas source 100, and the patient interface gas inlet port 81 is in fluid communication with the ventilator ventilation gas output port 38, such that compressed gas is provided by the external compressed gas source 100 to the ventilator 12 and ventilation gas is provided by the ventilator 12 to the patient interface 80 without passing through the compressor unit 14.

With the ventilatory support apparatus 10 of the exemplary embodiment in the stand-alone configuration, the ventilator 12 may be powered off by pressing the ventilator power button 20 in the same way as in the extended range configuration, e.g., by pressing the ventilator power button 20 for three seconds and confirming power off using the display 16 (e.g., as described on p. 40 of Appendix A). With the ventilator 12 powered off, the stand-alone range configuration can be terminated by disconnecting the compressed gas hose 84 from the ventilator 12 and the external compressed gas source 100.

As noted above, the ventilator 12 may include a wireless transmitter 31 and the compressor unit 14 may include a wireless receiver 79. In any of the above-described configurations (e.g. the stationary configuration, the extended range configuration, or the stand-alone configuration), the compressor 83 of the compressor unit 14 may be controllable by signal transmission from the wireless transmitter 31 to the wireless receiver 83 initiated by user input at the user interface 18. In this way, whether or not the ventilator 12 is docked with the compressor unit 14, the patient or another user of the ventilator 12 can wireless control the ventilatory support apparatus 10. Signal transmission between the wireless transmitter 31 and wireless receiver 83 may be according to any wireless communication standard known in the art. Alternatively, the ventilator 12 may communicate with the compressor unit 14 by a wired connection, in which case the wireless transmitter 31 and the wireless receiver 79 may be omitted. However, it may be seen that wireless communication may be advantageous, in that the ventilator 12 may be configured to control all electronically controllable aspects of the ventilatory support apparatus 10 in all configurations, without necessitating a separate set of controls on the compressor unit, and without requiring the presence of a wired signal link.

The ability to use the ventilatory support apparatus 10 in any one of the aforementioned configurations is attributable, at least in part, to the structural and functional features of its electromechanical pneumatic system which is under the control of a microprocessor. A pneumatic diagram of this system is provided on p. 142 of Appendix A. Along these lines, p. 142 of Appendix A sets forth the overall performance specifications of the ventilatory support apparatus 10 corresponding to its use in any of the aforementioned configurations.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

By way of example, it is contemplated that an alternative version of the ventilatory support apparatus 10 may be provided which is adapted to be used in only the stationary and extended range configurations, and is not necessarily adapted for use in the stand-alone configuration. In such a variation, structures and on-board control algorithms/software corresponding to functionality in such stand-alone configuration could be eliminated in the ventilatory support apparatus 10. Along these lines, it is also contemplated that an alternative version of the ventilatory support apparatus 10 may be provided which eliminates features such as the low flow gas input port 64 in the compressor unit 14, along with its ancillary structural and functional/control features. In this instance, with the elimination of the low flow gas input port 64 and the resultant inability to introduce, for example, oxygen directly into the compressor unit 14 via that low flow gas input port 64, it is further contemplated that such variant of the ventilatory support apparatus 10 may be used in conjunction with a patient interface which is uniquely configured to allow, for example, oxygen to be introduced directly into such patient interface from a suitable source.

What is claimed is:

1. A ventilatory support apparatus transitionable between a stationary configuration, an extended range configuration, and a stand-alone configuration, the ventilatory support apparatus comprising:
    a compressor unit, the compressor unit comprising:
        a compressor for providing compressed gas;
        a ventilator dock having a ventilator dock compressed gas output port;
    and a ventilator dock ventilation gas inlet port;
        a compressor unit ventilation gas output port; and
        a compressor unit compressed gas output port;
    a ventilator for providing ventilation gas, the ventilator being configured for removable docking at the ventilator dock, comprising:
        a ventilator ventilation gas output port; and
        a ventilator compressed gas inlet port;
    a patient interface for receiving ventilation gas and delivering ventilation gas to a patient, the patient interface having a patient interface gas inlet port transitionable between placement in fluid communication with the compressor unit ventilation gas output port and placement in fluid communication with the ventilator ventilation gas output port;
    wherein, when the ventilatory support apparatus is transitioned to the stationary configuration, the ventilator is docked at the ventilator dock, the ventilator compressed gas inlet port is in fluid communication with the ventilator dock compressed gas output port, the ventilator ventilation gas output port is in fluid communication with the ventilator dock ventilation gas inlet port, and the patient interface gas inlet port is in fluid communication with the compressor ventilation gas output port, such that compressed gas is provided by the compressor unit to the ventilator and ventilation gas is returned to the compressor unit for subsequent output from the compressor unit to the patient interface;
    wherein, when the ventilatory support apparatus is transitioned to the extended range configuration, the ventilator is not docked at the ventilator dock, the ventilator compressed gas inlet port is in fluid communication with the compressor unit compressed gas output port, and the patient interface gas inlet port is in fluid communication with the ventilator ventilation gas output port, such that compressed gas is provided by the compressor unit to the ventilator and ventilation gas is provided by the ventilator to the patient interface without being returned to the compressor unit; and
    wherein, when the ventilatory support apparatus is transitioned to the stand-alone configuration, the ventilator is not docked at the ventilator dock, the ventilator compressed gas inlet port is in fluid communication with an external compressed gas source, and the patient interface gas inlet port is in fluid communication with the ventilator ventilation gas output port, such that compressed gas is provided by the external compressed gas source to the ventilator and ventilation gas is provided by the ventilator to the patient interface without passing through the compressor unit.

2. The ventilatory support apparatus of claim 1, wherein the compressor unit further comprises a low flow gas input port.

3. The ventilatory support apparatus of claim 2, wherein the low flow gas input port comprises a low flow oxygen input port.

4. The ventilatory support apparatus of claim 1, wherein the compressor is configured to compress ambient air.

5. The ventilatory support apparatus of claim 4, wherein the compressor unit further comprises one or more ambient air apertures for introducing ambient air to the compressor.

6. The ventilatory support apparatus of claim 5, wherein the one or more ambient air apertures further comprises a filter.

7. The ventilatory support apparatus of claim 1, wherein the compressor unit compressed gas output port comprises a Diameter Index Safety System coupling.

8. The ventilatory support apparatus of claim 1, wherein the ventilator is electrically powered and includes a rechargeable battery.

9. The ventilatory support apparatus of claim 8, wherein the ventilator dock is configured to provide electrical power for powering the ventilator and for recharging the rechargeable battery when the ventilator is docked at the ventilator dock.

10. The ventilatory support apparatus of claim 1, wherein the ventilator further comprises a user interface and a wireless transmitter, wherein the compressor unit further comprises a wireless receiver, and wherein the compressor is controllable by signal transmission from the wireless transmitter to the wireless receiver initiated by user input at the user interface.

11. A ventilatory support apparatus transitionable between a stationary configuration and an extended range configuration, the ventilatory support apparatus comprising:
    a compressor unit, the compressor unit comprising:
        a compressor for providing compressed gas;
        a ventilator dock having a ventilator dock compressed gas output port;
    and a ventilator dock ventilation gas inlet port;
        a compressor unit ventilation gas output port; and
        a compressor unit compressed gas output port;
    a ventilator for providing ventilation gas, the ventilator being configured for removable docking at the ventilator dock, comprising:
        a ventilator ventilation gas output port; and
        a ventilator compressed gas inlet port;
    a patient interface for receiving ventilation gas and delivering ventilation gas to a patient, the patient interface having a patient interface gas inlet port transitionable between placement in fluid communication with the compressor unit ventilation gas output port and placement in fluid communication with the ventilator ventilation gas output port;
    wherein, when the ventilatory support apparatus is transitioned to the stationary configuration, the ventilator is docked at the ventilator dock, the ventilator compressed gas inlet port is in fluid communication with the ventilator dock compressed gas output port, the ventilator ventilation gas output, port is in fluid communication with the ventilator dock ventilation gas inlet port, and the patient interface gas inlet port is in fluid communication with the compressor ventilation gas output port, such that compressed gas is provided by the compressor unit to the ventilator and ventilation gas is returned to the compressor unit for subsequent output from the compressor unit to the patient interface; and
    wherein, when the ventilatory support apparatus is transitioned to the extended range configuration, the ventilator is not docked at the ventilator dock, the ventilator compressed gas inlet port is in fluid communication with the compressor unit compressed gas output port, and the patient interface gas inlet port is in fluid communication with the ventilator ventilation gas output port, such that compressed gas is provided by the compressor unit to the ventilator and ventilation gas is provided by the ventilator to the patient interface without being returned to the compressor unit.

12. The ventilatory support apparatus of claim 11, wherein the compressor is configured to compress ambient air.

13. The ventilatory support apparatus of claim 12, wherein the compressor unit further comprises one or more ambient air apertures for introducing ambient air to the compressor.

14. The ventilatory support apparatus of claim 13, wherein the one or more ambient air apertures further comprises a filter.

15. The ventilatory support apparatus of claim 11, wherein the compressor unit compressed gas output port comprises a Diameter Index Safety System coupling.

16. The ventilatory support apparatus of claim 11, wherein the ventilator is electrically powered and includes a rechargeable battery.

17. The ventilatory support apparatus of claim 16, wherein the ventilator dock is configured to provide electrical power for powering the ventilator and for recharging the rechargeable battery when the ventilator is docked at the ventilator dock.

18. The ventilatory support apparatus of claim 11, wherein the ventilator further comprises a user interface and a wireless transmitter, wherein the compressor unit further comprises a wireless receiver, and wherein the compressor is controllable by signal transmission from the wireless transmitter to the wireless receiver initiated by user input at the user interface.

19. A method for transitioning a modular ventilatory support apparatus from one to another of a stationary configuration, an extended range configuration, and a stand-alone configuration, the method comprising:
    providing a modular ventilatory support apparatus comprising:
        a compressor unit comprising a compressor for providing compressed gas, a low flow oxygen input port, a compressor unit ventilation gas output port, a compressor unit compressed gas output port, and a ventilator dock, the ventilator dock having a ventilator dock compressed gas output port and a ventilator dock ventilation gas inlet port;
        a ventilator configured for removable docking at the ventilator dock, the ventilator comprising a user interface, a ventilator ventilation gas output port, and a ventilator compressed gas inlet port; and
        a patient interface having a patient interface gas inlet port transitionable between placement in fluid communication with the compressor unit ventilation gas output port and placement in fluid communication with the ventilator ventilation gas output port; and
    transitioning the modular ventilatory support apparatus from one to another of a stationary configuration, an extended range configuration, and a stand-alone configuration;
    wherein the modular ventilatory support apparatus is transitioned to the stationary configuration when the ventilator is docked at the ventilator dock with the ventilator compressed gas inlet port placed in fluid communication with the ventilator dock compressed gas output port and with the ventilator ventilation gas output port placed in fluid communication with the ventilator dock ventilation gas inlet port, and the patient interface gas inlet port is placed in fluid communication with the compressor ventilation gas output port, such that compressed gas is provided by the compressor unit to the ventilator and ventilation gas is returned to the compressor unit for subsequent output from the compressor unit to the patient interface;

wherein the modular ventilatory support apparatus is transitioned to the extended range configuration when the ventilator is not docked at the ventilation dock, the ventilator compressed gas inlet port is placed in fluid communication with the compressor unit compressed gas output port, and the patient interface gas inlet port is placed in fluid communication with the ventilator ventilation gas output port, such that compressed gas is provided by the compressor unit to the ventilator and ventilation gas is provided by the ventilator to the patient interface without being returned to the compressor unit; and wherein the modular ventilatory support apparatus is transitioned to the stand-alone configuration when the ventilator is not docked at the ventilation dock, the ventilator compressed gas inlet port is placed in fluid communication with an external compressed gas source, and the patient interface gas inlet port is placed in fluid communication with the ventilator ventilation gas output port, such that compressed gas is provided by the external compressed gas source to the ventilator and ventilation gas is provided by the ventilator to the patient interface without passing through the compressor unit.

20. The method of claim 19, wherein the compressor is configured to compress ambient air.

* * * * *